(12) United States Patent
Manwaring et al.

(10) Patent No.: US 6,214,019 B1
(45) Date of Patent: Apr. 10, 2001

(54) CONVERGENT MAGNETIC STEREOTAXIS SYSTEM FOR GUIDANCE TO A TARGET

(75) Inventors: Kim H. Manwaring, Provo, UT (US); Mark L. Manwaring, Pullman, WA (US)

(73) Assignee: Brain Child Foundation, Carefree, AZ (US)

( * ) Notice: Subject to any disclaimer, the term of this patent is extended or adjusted under 35 U.S.C. 154(b) by 0 days.

(21) Appl. No.: 09/349,524

(22) Filed: Jul. 8, 1999

(51) Int. Cl.[7] ................................................ A61B 19/00
(52) U.S. Cl. ............................................................ 606/130
(58) Field of Search .................................. 606/129, 130; 600/114, 117

(56) References Cited

U.S. PATENT DOCUMENTS

| 3,731,752 | * | 5/1973 | Schad | 175/45 |
| 3,822,694 | * | 7/1974 | Mills | 600/407 |
| 4,079,730 | * | 3/1978 | Wikswo, Jr. et al. | 600/504 |
| 4,176,662 | * | 12/1979 | Frazer | 600/114 |
| 4,608,992 | * | 9/1986 | Hakim et al. | 600/431 |
| 4,739,771 | | 4/1988 | Manwaring . | |
| 4,927,420 | | 5/1990 | Newkirk et al. . | |
| 4,955,389 | * | 9/1990 | Schneider | 600/554 |
| 5,122,138 | | 6/1992 | Manwaring . | |
| 5,258,755 | * | 11/1993 | Kuckes | 340/853.5 |
| 5,566,681 | | 10/1996 | Manwaring et al. . | |
| 5,711,299 | | 1/1998 | Manwaring et al. . | |
| 5,762,064 | * | 6/1998 | Polvani | 600/424 |
| 5,769,843 | * | 6/1998 | Abela et al. | 606/10 |
| 6,052,610 | * | 4/2000 | Koch | 600/424 |

* cited by examiner

Primary Examiner—Gene Mancene
Assistant Examiner—Eduardo C. Robert
(74) Attorney, Agent, or Firm—Mayer, Brown & Platt

(57) ABSTRACT

A guidance system for guiding a surgical instrument without visual information to a target in tissue. The system centers the target upon the trajectory of an infinite family of zero-flux curvilinear lines emanating from either a fixed magnet or an ac or dc electromagnet which is mounted on the instrument. The approach to the target allows selection of straight and curved trajectories based on the zero-flux lines that intersect the target. A self-centering attachment that holds the magnet allows any straight instrument to be guided by the system. The zero-flux lines are measured by a magnetometer that is located on a remote location on or in the tissue. The transducers of the magnetometer measure the magnetic field strength that is present if the instrument deviates from the zero-flux line. The guidance information is plotted on a display that allows a user to guide the instrument along the zero-flux line to the target. An alternative embodiment uses a sensing magnetometer in the instrument tip that measures the field strength that is generated from a magnet that is placed on a remote location on or in the tissue.

28 Claims, 8 Drawing Sheets

CONVERGENT MAGNETIC STEREOTAXIS SYSTEM FOR GUIDANCE TO A TARGET

FIELD OF INVENTION

The invention relates to a method and apparatus for directing a surgical instrument to a target location. More specifically, the invention relates to using a magnet and a magnetometer to guide the instrument on zero-flux lines to the target location.

BACKGROUND OF THE INVENTION

A wide variety of medical and surgical procedures are optimally performed for best diagnostic or therapeutic efficacy when a surgical instrument is passed through tissue precisely to a target location. Common examples of these procedures include biopsy of suspected abnormal tissue or placement of a ventriculostomy or shunt catheter into the brain in the treatment of hydrocephalus. Techniques to allow improved guidance or positioning have been developed. However, these techniques all suffer from significant shortfalls.

Exemplifying these shortfalls are the techniques which may be used for the placement of a shunt catheter into the brain for treatment of hydrocephalus. Hydrocephalus is a disease principally of malabsorption of cerebrospinal fluid (CSF) that results in the gradual enlargement of the ventricles in the brain with effacement and eventual permanent injury to adjacent tissues. It is most commonly treated by drilling a hole in the skull and guiding a silicone shunt catheter or ventriculostomy tube into the ventricle. The cerebrospinal fluid is diverted from its normal and impeded path through the catheter. The shunt apparatus is usually further tunneled beneath the skin of scalp and body to terminate in the peritoneal cavity (VP shunt) or in the atrium of the heart (VA shunt) in order to direct the CSF to the body's circulatory system. The long-term success or control of hydrocephalus depends on proper positioning of the catheter. Misplacement of the catheter may lead to acute obstruction of the tube with brain tissue or delayed obstruction due to gradual ingrowth of choroid plexus. The obstructions then require that the catheter be replaced by additional surgery.

To minimize the risk of malposition, a surgeon has several options. For example, well-described, externally palpable landmarks of the cranium may be used to select and drill a hole. The catheter is then aimed toward another palpable landmark of the head, expecting to intersect an optimal target location at a depth judged from review of imaging studies such as computed tomography (CT) and magnetic resonance imaging (MRI). However, this technique is difficult to employ due to human variation in landmarks, variability in the ventricle size and position, and encumbrance of surgical drapes used to isolate a surgical field. Malposition attributable to these variables is a common complication.

Alternatively, real time ultrasound may be employed to guide a catheter precisely in infants through an open fontanel. However, the fontanel is normally closed after 18 months of age, forcing the creation of an otherwise unnecessary burr hole to image the brain at an older age.

A stereotaxic frame may also be employed to guide a catheter precisely, but this requires lengthy acquisition of target coordinates in a radiologic suite before surgery. The application of the frame is also an invasive procedure, since the frame is installed with a series of pins which are inserted into the cranium. Similarly, the more recent techniques of "frameless stereotaxy" require pre-operative localization of fiducials or markers for orientation and employ costly equipment for a simple procedure.

Intraoperative CT and MRI (so-called open MRI) allow precise guidance, but the necessary equipment for these procedures present significant hindrances to sterile setup, timely operation, operating room efficiency, and cost since such equipment is not ordinarily used in the operating room. These techniques also operate by emitting ionizing energy which may have cumulative potential injurious effect in the case of CT or interfering magnetic fields in the case of MRI.

Endoscopic adjunctive guidance of the shunt catheter facilitates final placement, but does not improve the trajectory accuracy through the soliditissue of the brain, the principal determinant of eventual position. Internal visual confirmation is also not normally necessary in the management of simple hydrocephalus.

A variety of external alignment devices have been developed. For example, the Ghajar guide, manufactured by Codman and Shurtleff of Raynham, Mass., is a guide tube which assures perpendicularity to the cranium. However, the Ghajar guide provides no depth control and requires a paramedian coronal entry burr hole. The guide also does not compensate for human variations of cranium or ventricle configuration and thus may result in malposition.

Thus, there exists a need for a catheter positioning device which: a) is simple, requiring minimal setup time, expense, training or expertise of the surgeon; b) allows precise guidance during surgery despite encumbrance of surgical drapes and difficulty at palpation of common landmarks; c) allows optimal target selection based on pre-operative imaging studies such as CT and MRI of the head; d) avoids invasiveness of a frame application to the patient or special imaging procedures to allow such guidance; and e) builds on the existing standards for the surgical approach to the ventricle system.

It is also desirable to have a guidance device which may be coupled to an endoscope or any other surgical instrument, allowing guidance to the target such that additional procedures such as biopsy or diagnostic ventriculoscopy may be performed with equal precision. A guidance technology which allows "on the fly" selection of alternative entry sites in the instance of recognized impediments in the path, e.g., a large vessel on the brain surface which should not be cut, is needed. There is also a need for a guidance device which allows a user to choose a minimal or a significantly curved trajectory toward a target rather than a straight line as forced by most of the aforementioned techniques. It would also be advantageous to rely on internal or within the body alignment instead of reference to external prominences, measured relationships, frames, line of sight or sound digitizers.

SUMMARY OF THE INVENTION

The above needs and problems are solved by the present invention, which is embodied in a guidance system for use in conjunction with an instrument having a substantially straight portion and a tip. The system determines the path of the instrument to a target area within tissue. The system has a magnet which is mounted on the substantially straight portion of the instrument and which emits a magnetic field with a family of zero-flux lines perpendicular to isogaussian planes. The target area is intersected by a selected zero-flux line. A self-centering housing may be coupled to the substantially straight portion of the surgical instrument and holds the magnet such that the magnetic center is aligned with the instrument. A magnetometer is placed in or on a remote tissue site in approximate alignment with the target area. The magnetometer includes an x-plane transducer, a y-plane transducer and a z-plane transducer. A guidance circuit is coupled to the transducer array and indicates when the magnet deviates from the selected zero-flux line.

The invention also is embodied in a method of guiding an instrument to a target area within tissue. A magnetometer having x- y- and z-plane transducers is affixed within or upon the tissue surface in approximate alignment with the target area and an anticipated trajectory from an outside fixed entry site. A magnet emitting a magnetic field is attached to the instrument. The instrument is inserted into the tissue at a fixed entry site. The location of the instrument is determined relative to the target area by measuring the flux lines of the magnetic field.

The invention is also embodied in a guidance system for use in conjunction with a surgical instrument having a tip which is inserted in tissue. The system determines the arrival of the tip of the surgical instrument at a target area within the tissue. The system has a magnetometer in the instrument tip. The magnetometer includes an x-plane transducer, a y-plane transducer and a z-plane transducer. A magnet which emits a magnetic field with a family of zero-flux lines perpendicular to isogaussian planes is provided. The target area is intersected by a selected zero-flux line. The magnet is located on a remote tissue site in approximate alignment with the target area. A guidance circuit is coupled to the transducer array which indicates when the magnet deviates from the selected zero-flux line.

The invention is additionally embodied in a method of guiding an instrument with a tip with a magnetometer having x-, y- and z-plane transducers to a target area within tissue. A magnet is affixed within or upon the body surface in approximate alignment with the target area and an anticipated trajectory from an outside fixed entry site. The instrument is inserted into the tissue. The location of the instrument is determined relative to the target area by measuring the flux lines of the magnetic field.

It is to be understood that both the foregoing general description and the following detailed description are not limiting but are intended to provide further explanation of the invention claimed. The accompanying drawings, which are incorporated in and constitute part of this specification, are included to illustrate and provide a further understanding of the method and system of the invention. Together with the description, the drawings serve to explain the principles of the invention.

DETAILED DESCRIPTION OF THE PREFERRED EMBODIMENT

Figure 1:
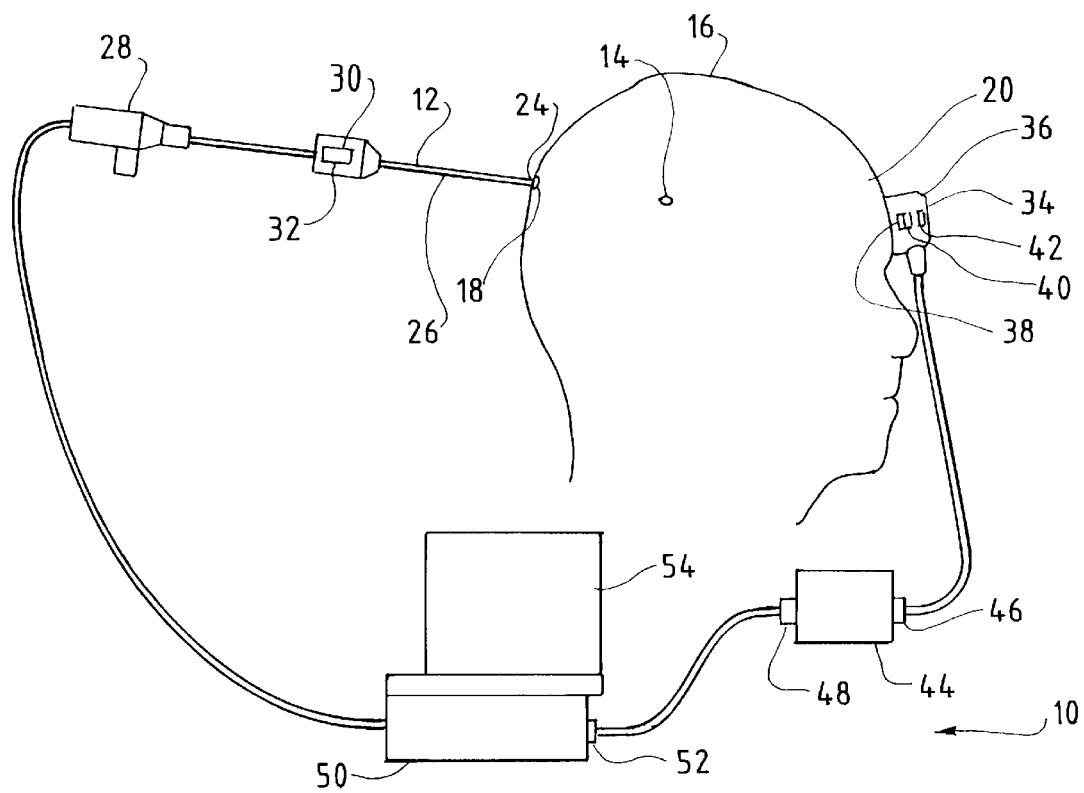
FIG. 1 is a perspective view of the guidance system according to the present invention used in conjunction with a medical instrument inserted into a cranium.

While the present invention is capable of embodiment in various forms, there is shown in the drawings and will hereinafter be described a presently preferred embodiment with the understanding that the present disclosure is to be considered as an exemplification of the invention, and is not intended to limit the invention to the specific embodiment illustrated.

One example of the present invention will now be explained with reference to FIG. 1, which shows a guidance system 10. The guidance system 10 is used to guide an instrument 12 to a target location or area 14 within a patient's cranium 16. The cranium 16 has a burr hole 18 that is drilled by a surgeon for surgical procedures. The cranium 16 has a midline forehead area 20 and a right occiput where the burr hole 18 is drilled. As will be explained, the burr hole 18 may be drilled at any convenient surface on the cranium 16 relative to the target location 14.

The instrument 12 has a tip 24 that is inserted in the cranium 16. The instrument 12 is an endoscope in this example, although any straight instrument such as a stylet for a catheter or a biopsy probe or needle may be used with the system 10 of the present invention. The instrument 12 has a substantially straight portion such as shaft 26, which has one end coupled to the tip 24. The other end of the shaft 26 is coupled to an endoscope camera 28. The guidance system 10 includes a magnet 30 that is mounted in a self-centering housing 32 that is attached to the instrument 12 on the straight shaft 26 at a set distance from the tip 24. A magnetometer 34 is placed in a typical supraglabellar location in the midline forehead area 20 of the cranium 16 to detect the emitted magnetic field from within the self-centering housing 32 from the magnet 30 mounted on the instrument 12. The placement of the magnetometer 34 is merely for illustrative purposes. The magnetometer 34 may be placed in or on any remote tissue site in appropriate alignment with the target 14.

The magnetometer 34 is a concentric design with a transducer array 36 having concentric x-, y- and z-plane transducers 38, 40 and 42. Each transducer 38, 40 and 42 senses magnetic field strength from the magnet 30 in a different plane. The transducers 38, 40 and 42 are fluxgate type transducers, although other types of transducers such as magneto-resistive sensors may be used. Alternatively, the transducers 38, 40 and 42 may be located as an in-line configuration within the magnetometer 34. The magnetometer 34 in this example is a Model 533 Miniature 3-axis Fluxgate Magnetometer, manufactured by Applied Physics Systems of Mountain View, Calif. or a HMR2300 Smart Magnetometer, manufactured by Honeywell of Minneapolis, Minn. However, other magnetometers may be used.

The instrument 12 is inserted in the burr hole 18 on the cranium 16. Once the surgeon elects a fixed entry site such as the burr hole 18, this becomes a pivot point to guide the instrument 12 along a defined zero-flux line from the magnet 30 measured by the magnetometer 34 to the target area 14 as will be explained below. The magnetometer 34 is coupled to a data interface device 44 via a data input 46. The data interface 44 in this example is a 21X Datalogger manufactured by Campbell Scientific, Incorporated of Logan, Utah. However, any data interface that is capable of real time earth magnetic field measurement and subtraction from the emitted magnetic field of a magnet may be used. The data interface 44 may be eliminated if a digital magnetometer with signal processing capability is used such as the HMR2300 digital magnetometer manufactured by Honeywell. The data taken from the magnetometer 34 is output via a data output port 48.

The data interface device 44 is coupled to a guidance circuit such as a computer 50 via a RS232 port 52. The interface device 44 controls sampling of the x, y, and z plane transducers 38, 40 and 42 of the magnetometer 34 as well as measurement of magnetic fields from the magnet 30. Analog-digital conversion of the data output of the magnetometer 34 is performed by the interface device 44. Alternatively, the digital output is available directly out of a digital magnetometer such as the Honeywell Smart Magnetometer HMR. The computer 50 also has a video input coupled to the output of the endoscope camera 28. The computer 50 is coupled to a display device 54 and includes appropriate software and hardware to generate the screen display as will be explained below with reference to FIG. 4.

Figure 2:
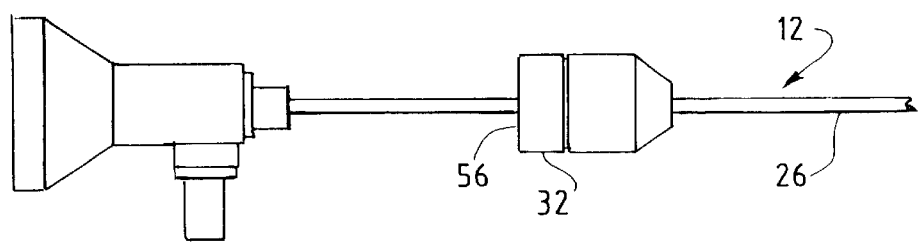
FIG. 2 is a perspective view of a self-centering housing for a magnet according to the present invention.
Figure 3:
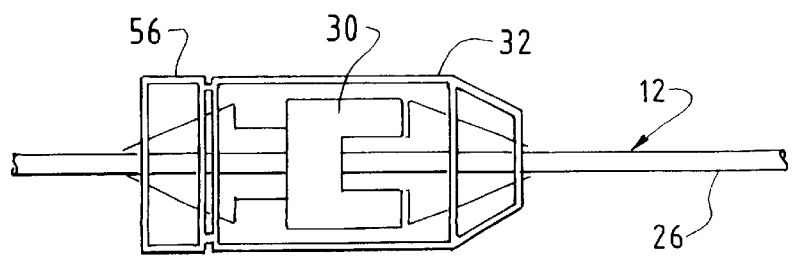
FIG. 3 is a cross-section view of the self-centering housing of the present invention.

FIG. 2 is a perspective view and FIG. 3 is a cross sectional view of the self-centering housing 32 mounted on the shaft 26. The self-centering housing 32 is identical in design to a common drill bit stop. The housing 32 has an interior shape to contain a centered horseshoe or U-shaped magnet such as magnet 30. As is well known, the poles of the magnet 30 are at the ends of the arms of the "U" shape. The arms of the magnet 30 are parallel to the shaft 26. An alnico horseshoe magnet is preferred because of increased forward field strength.

Alternatively, a bar magnet may be used instead of a horseshoe magnet. Such a bar magnet would be mounted perpendicularly to the shaft 26 to place the poles in a similar position as those of a horseshoe magnet. Alternatively, the magnet 30 may be an electromagnet. The electromagnet is energized by either a DC current, a pulsed DC current or an AC current. While common ceramic magnets can be employed for the magnet 30, much stronger magnets such as alnico or rare earth magnets are preferable to optimize measurement of a zero-flux line by the magnometer 34. Similarly, an alternating field could be obtained by rotating the magnet within the housing using a small rotary motion source such as a wind-up motor or electric motor.

The magnet 30 may also be a standard magnet such as the General Tools Part No 372A (a permanent button alnico magnet), manufactured by General Tools Manufacturing Company, Inc. of New York, N.Y. The system 10 may be used effectively with the fixed magnet approach, but without the benefit of real time subtraction of the earth's field or sources of interference by the data interface 44 during instrument passage in the surgical environment.

The housing 32 is positioned on the straight portion 26 of the instrument 12 at a depth from the tip 24 roughly at the estimated depth from burr hole 18 to the target area 14. The position of the housing 32 on the straight portion 26 may be measured by a common surgical ruler as a safety precaution in use. This prevents over insertion of the instrument 12 into the cranium 16. The housing 32 is coupled to the straight portion 26 by an annular snugging ring 56. The snugging ring 56 may be rotatably adjusted to fix the housing 32 on any position on the straight portion 26. When the snugging ring 56 is loosened, the housing 32 may be moved to different positions on the straight portion 26 relative to the tip 24 of the instrument 12. The system 10 may be used with any instrument with a relatively straight portion, which allows the installation and adjustment of the housing 32.

The center of the horseshoe or U-shaped magnet 30 is positioned on the center axis of the instrument 12. Thus, the center line of the endoscope shaft 26 and the housing 32 are coincident. Alternatively, a miniature magnet mounted in the tip 24 of the instrument 12 may be used instead of the magnet 30 and the housing 32 if greater accuracy is desired.

Figure 4:
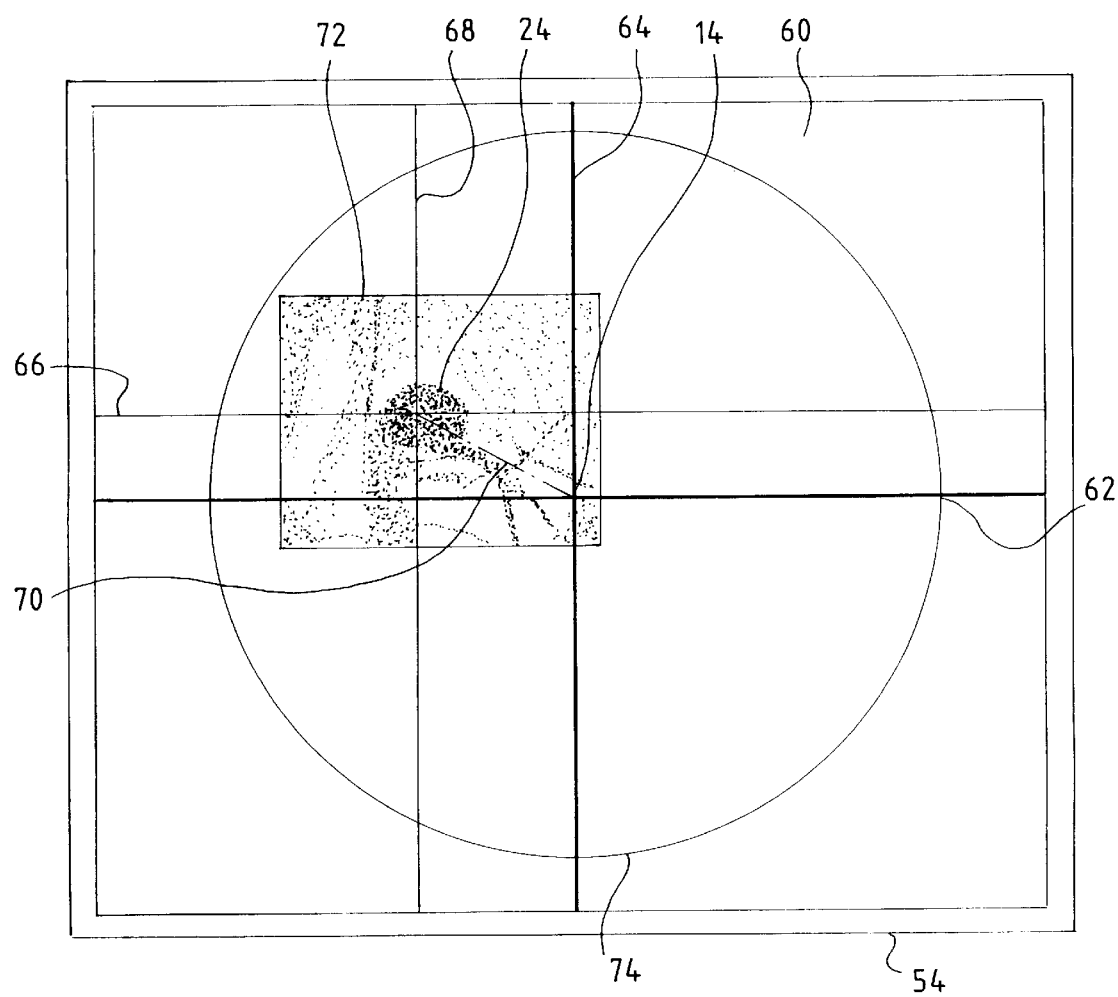
FIG. 4 is a guidance display screen that shows guidance data obtained according to the present invention.

FIG. 4 shows an optical feedback screen 60 as presented on the display device 54 during the traversal of the tip 24 of the instrument 12 through tissue to the target 14 in FIG. 1. The display device 54 is preferably a liquid crystal display since no significant magnetic field is emitted, allowing the display device 54 to be placed directly in a position in proximity to the instrument 12. Alternatively, a conventional cathode ray tube display may be positioned at least 1 meter away from the magnet 30 to diminish any magnetic field interference.

The screen 60 includes a pair of glidepath cross hairs 62 and 64. Glidepath cross hair 62 is the x (left-right instrument tip position) axis and glidepath cross hair 64 is the y (up-down instrument tip position) axis. The glidepath cross hairs 62 and 64 are centered on the screen 60, indicating the surgeon's ideal glidepath down a zero-flux line to the target 14. The deviation of the tip 24 of the instrument 12 off of the glidepath is indicated by tip location cross hairs 66 and 68 which are the x and y axes respectively. A magnet plane is plotted as a compass heading line 70 extending out of the guideline cross hairs 62 and 64. Using the tip location cross hairs 66 and 68, a surgeon "pulls" the tip 24 of the instrument 12 back physically to align the tip with the glidepath cross hairs 62 and 64 much as a skeet shooter sites his gun and pulls the barrel back on target.

The orientation of the magnetic field emitted by the magnet 30 is shown on the screen 60 by the compass line 70 extending out from the intersection of the glidepath cross hairs 62 and 64. The direction of the compass line 70 is derived from arctan y/x where y is derived from the y-plane transducer 40 and x is derived from the x-plane transducer 38. The compass line 70 represents the orientation of the magnet 30 in either the x or y plane to allow for correction of the instrument trajectory.

An endoscope image 72 of tissue taken from the tip 24 of the endoscope instrument 12 is transmitted by the endoscope camera 28 and is centered on the intersection of the actual location cross hairs 66 and 68 by the computer 50. When the tip 24 reaches the depth of the target 14, an enlarging concentric circle 74 matches the diameter of the endoscope image 72. The concentric circle 74 enlarges in diameter as the instrument 12 nears the target 14. This yields a 3-dimensional subjective effect of target approach of the instrument 12 on the screen 60. The correct positioning of the tip 24 at the target 14 is thus indicated by centering the endoscope image 72 and location cross hairs 66 and 68 on the glidepath cross hairs 62 and 64 and matching the diameter of the endoscope image 72 to the diameter of the concentric circle 74.

The operation of the system 10 according to the present invention will now be explained with reference to FIGS. 1–4 and FIG. 5 which shows a pattern of flux lines 100 which emanate from the magnetic center of a bar magnet 102 as concentric ellipses approximating circles. The flux lines 100 represent isogaussian planes of field density, diminishing in strength with distance from the center of the magnet 102. A simple, fixed magnet (or an electromagnet) emits a magnetic field with a shape that is influenced by the magnet's geometry and the alignment orientation of its magnetic domains. This pattern depicts the approximate shape of isogaussian distributional, though the exact shape is normally slightly more shortened in the perpendicular plane away from the magnet 102. The depiction in FIG. 5 also approximates a pattern for a horseshoe or U-shaped magnet such as the magnet 30 in FIG. 1.

Figure 5:
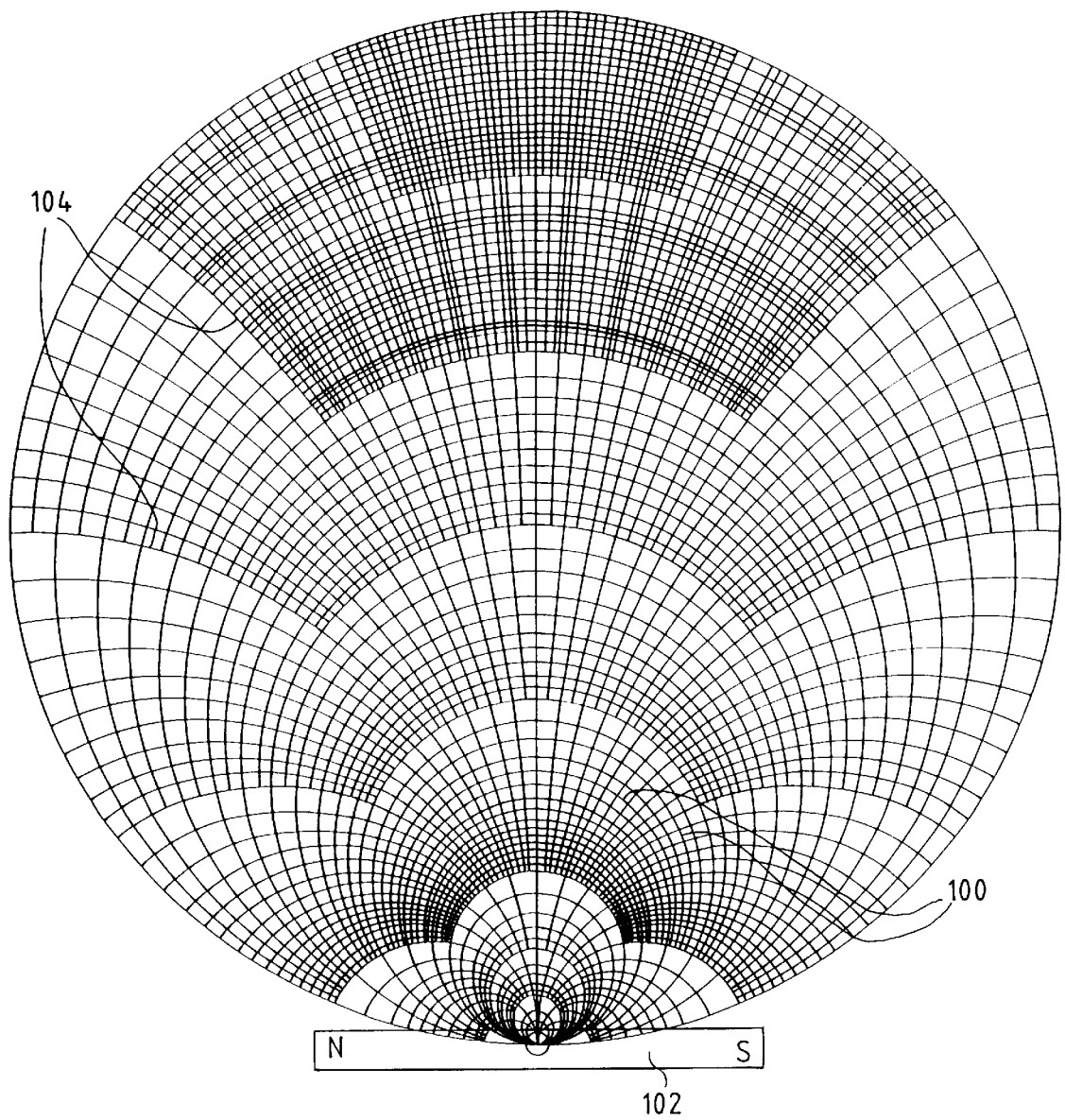
FIG. 5 is a chart of flux lines and perpendicular "zero-flux" trajectories of a magnet used by the present invention.

The pattern of a constant, pulsed, or continuously alternating magnetic flux distribution at a given point in time is thus represented in FIG. 5. The strength of a magnetic field emanating from a magnet 102 will be constant on any flux line 100 as measured by the magnetometer 34 in FIG. 1 if the magnetometer transducers 38, 40 or 42 are oriented tangentially to the elliptical line.

A perpendicular line extending from the center of the magnet and intersecting the flux lines 100 at right angles to the elliptical or near circular flux line defines a "zero-flux line" 104. The strength of a magnetic field emanating from the magnet 102 will always be zero on a zero-flux line 104 as measured by the magnetometer 34 if the z-plane transducer 42 remains oriented perpendicular to the line 104. Misalignment to the zero-flux line 104 will result in a measurable positive or negative magnetic field strength in the z-plane transducer 42. The deviation in field strength is displayed on the screen 60 to indicate direction and magnitude of required correction to re-align directly on the zero-flux line 104, which represents the glidepath to the target. The z-plane transducer 42 in the magnetometer 34 is aligned perpendicularly to a given zero-flux line such as flux line 104. The x- and y-plane transducers 38 and 40 will measure full intensity of the magnetic flux from the magnet 102 depending on the rotation of the magnet 102. As the instrument 12 is advanced down a zero-flux line such as flux line 104, it will eventually intersect the magnetic center of the magnet 102, thus providing an exact path to the magnetometer 34. If a target in the tissue is aligned with the magnetometer, it may be exactly intersected.

The magnet 30 in FIG. 1–3 will emit a symmetrical field in an x axis when oriented horizontally very similar to the field depiction in FIG. 5 due to its position. The y axis orientation is obtained by rotating the magnet 30 along with the housing 32 by 90 degrees to the vertical position. This allows feedback measurement of the maximum and minimum flux density by the x- and y-plane transducers 38 and 40 of the magnetometer 34 for orientation in the y plane as seen in compass line 70. The rotation of the magnet 30 must be performed periodically to assure passage on a zero flux lines in both the x and y planes. The orientation change may be automated by use of a mechanically rotated magnet or by pulsing of housed electromagnets with sine waves 90 degrees out of position with each other.

Alternatively, if the magnet 30 within the housing 32 on the instrument 12 is rotated in real time by a wind-up or electrical motor, sampling and plotting are performed automatically at peak points of x and y magnetometer measurement of flux density. The automated display coupled with a rotating field eliminates the need for the surgeon to rotate the magnet physically to check alignment in both planes of the glidepath.

The glidepath cross hairs are generated on the screen 60 from the output of the z-plane transducer 42 when the magnet 30 is oriented in the x and y planes respectively by software deriving data from the data interface 44.

The tip location cross hair 68 is derived in the x plane and generated on the screen 60 by measuring the magnetic field deviation away from the zero-flux line (or value of zero) using the z-plane transducer 42 of the magnetometer 34. The measured deviation is plotted either left or right of the guidance cross hair 64 by amplitude on the x plane. The point is plotted when the x-plane transducer 38 reads a maximum flux density and the y-plane transducer 40 reads a minimal flux density simultaneously.

Conversely, the tip location cross hair 66 is generated by measuring the deviation off of the glidepath in the y plane. The deviation away from the zero-flux line (or value of zero) on the z-plane transducer 42 of the magnetometer 34 is measured. This value is plotted above or below the guideline cross hair 62 by amplitude on the y plane. The point is plotted when the y-plane transducer 40 reads a maximum flux density and the x-plane transducer 38 reads a minimal flux density simultaneously.

The plots are accomplished by software running by the computer 50. Plotting software such as LabTech Control manufactured by LabTech Corporation in Wilmington, Mass., may be used to generate the screen 60. Of course any appropriate software program may be used to read the magnetic field data and generate the screen 60. Appropriate video hardware and software are used to display endoscope image 72 on the screen 60.

Better accuracy for traversal of a zero-flux line is gained by using a straight instrument such as an endoscope with the shortest possible length between the tip and the housing 32. This is due to the perpendicularity of the zero-flux line at intersection with the tangent of the near circular ellipses. In practice, this is a minor limitation as accuracy improves as the instrument approaches the target due to convergence of zero-flux lines toward the magnetometer.

In order to guide the instrument tip 24 along a zero-flux line as detected by the magnetometer 34, it is necessary to cancel out the earth's magnetic field effect and to eliminate, control for, or subtract out sources of magnetic interference in the surgical environment. Since the technique of converging accuracy as described above embodies the element of increasing magnetic field strength as the target 14 is approached, minimal interference is encountered in the normal surgical environment. This is due to conventional use of non-magnetic stainless steel instruments and sufficient distance from substantial ferromagnetic material, such as iron and steel in operating tables and microscope bases. It is only necessary in normal practice to zero the magnetometer with the instrument and housing containing the magnet at least 1 meter removed from the surgical field. Current surgical practice demonstrates convergence on the magnetometer as a target to within 1 mm when this guideline is employed.

Yet another approach yields similar accuracy based on convergence of zero-flux lines as the target is approached. The entry burr hole site 18 is touched by the instrument 12 and housing 32 containing the magnet 30 in correct orientation. The instrument 12 is aimed by visual alignment technique to the target 14, estimating its internal location. The magnetometer 34 is then zeroed by subtracting existing flux values out to a value of zero. As the instrument 12 is further advanced into the cranium 16, deviation off of a zero flux line to the magnetometer 34 as a target is easily recognized and guidance is performed identically as above, obtaining similar accuracy.

Real time earth and interference subtraction during passage of the instrument 12 to the target 14 may also be achieved by using a compensation circuit that uses paired electromagnet excitation and magnetometer sampling with earth subtraction or field reversal as taught in the inventors' U.S. Pat. Nos. 5,638,819, 5,711,299 and 5,891,158, which are hereby incorporated by reference.

Figure 6:
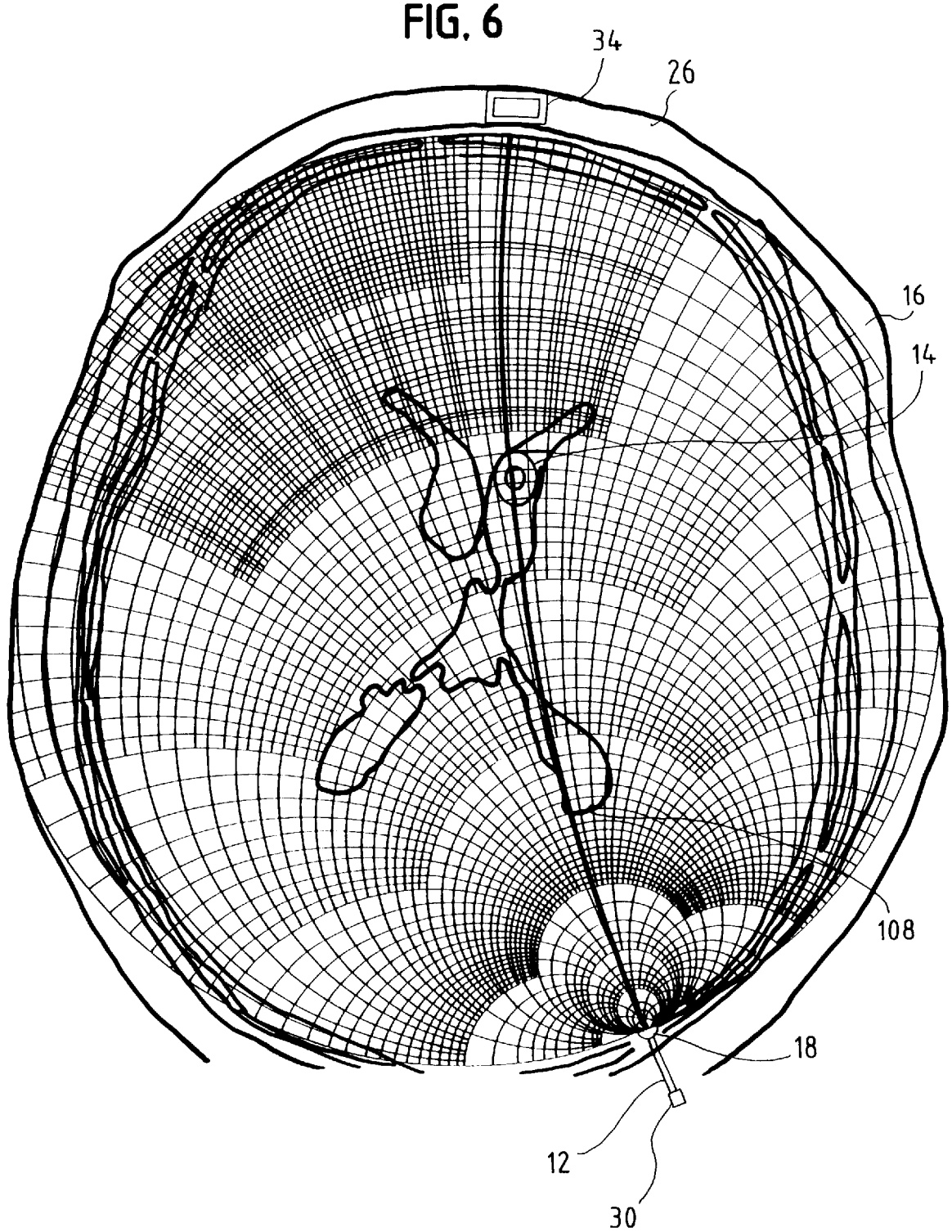
FIG. 6 is an axial MRI scan showing the orientation of flux lines and placement of the magnetometer for application of the present invention.

Typically, an approach to the target 14 is selected using imaging studies. In this example, the surgeon has elected a posterior cranial approach to the target 14. FIG. 6 is an axial MRI scan of the cranium 16 showing the target 14 and selected zero-flux lines leading toward the target 14 and the magnetometer 34. As the magnetic field permeates the cranium 16 and soft tissues of scalp and brain without impediment, a zero-flux trajectory line 108 to the target is detectable within and outside the cranium 16. The magnetometer 34 is placed on the midline forehead area 20 due to size and external electrical connections. The magnetometer 34 is on the selected zero-flux line 108 downpath from the target 14 and the magnet 30 and its magnetic field.

If the surgeon encounters an impediment in the path, such as an overlying vital vessel, he can move to an adjacent or removed site, so long as a zero-flux line intersects this region, which will also guide him to the target. A distinct advantage of this invention is the wide latitude of options presented to the surgeon requiring only geographic approximation of an entry site to allow convergence on the target as illustrated in FIG. 6. Further, a curved path may be elected if it offers advantages compared to a relatively straight path. The emitted magnetic field zero-flux line 108 as detected by the magnetometer 34 is a curved trajectory line converging on the target 14 as illustrated in FIG. 6. In addition, multiple consecutive or simultaneous paths to the same target may be employed for multiple instruments without additional planning.

Figure 7:
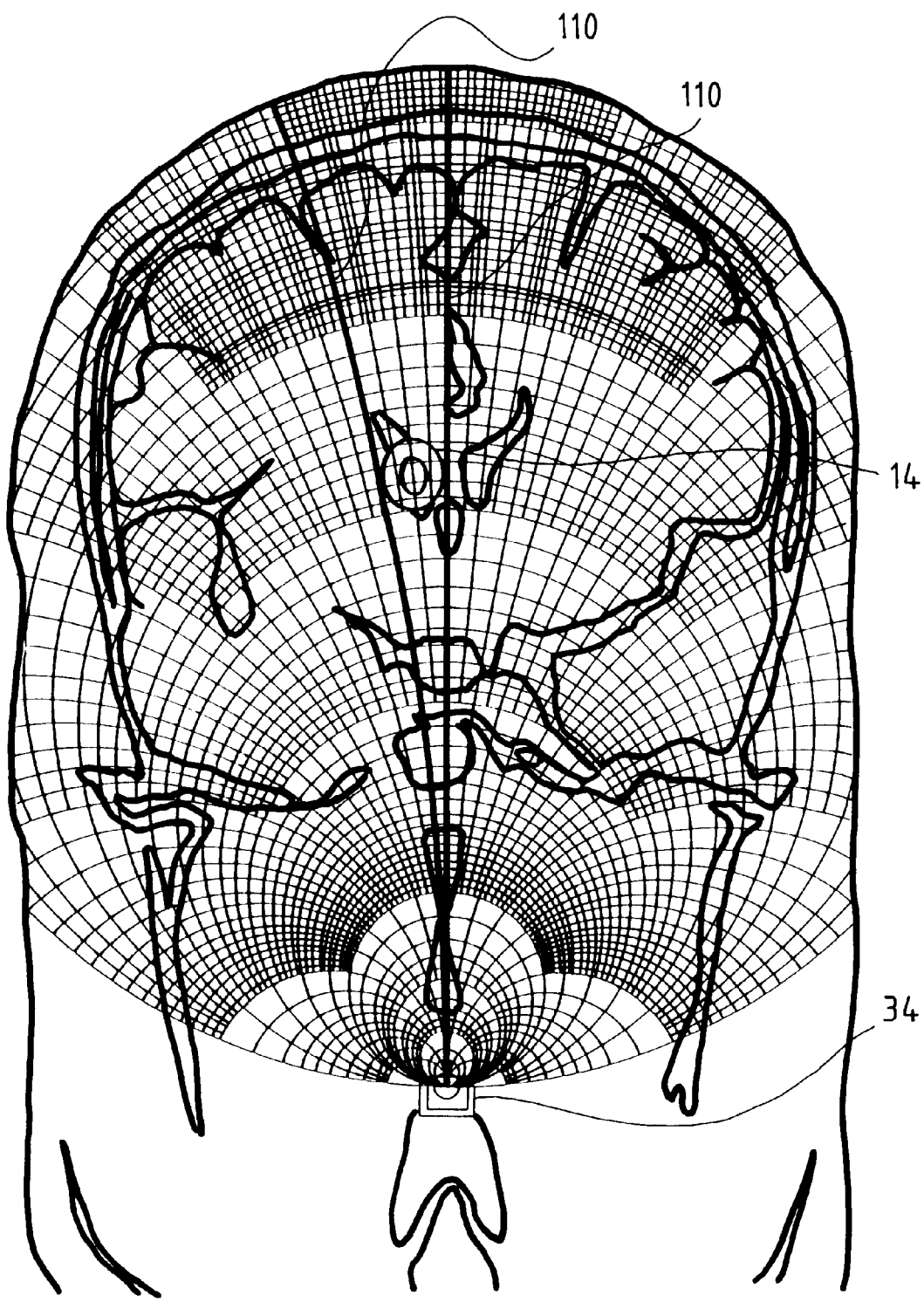
FIG. 7 is a coronal MRI scan of the brain showing a family of "zero-flux lines" and an alternate placement of the magnetometer for application of the present invention.

An example of an alternative approach to an intracranial target is shown in FIG. 7, which is an MRI scan of a typical coronal cut of the brain. This approach employs the same elements as the system 10 in FIGS. 1–4. The target 14 is in the identical location of a frontal horn of the lateral ventricles in the cranium 16 as the view in FIG. 6. The magnetometer 34 is placed in the anesthetized patient's mouth against the soft palate and dorsal to the typical location of an endotracheal tube. The surgeon can elect a family of zero-flux lines 110 that will offer a trajectory within the confines of the target space to its intersection. The depth from a coronal burr hole on the top of the head to the target may be measured by conventional, readily available techniques in the radiologic suite from CT or MRI type images.

Depth to the target 14 may also be indicated by measuring increasing field strength in the two x and y-plane transducers 38 and 40 in the magnetometer 34. The third z-plane transducer 42 in the magnetometer 34 measures flux in the direction toward the instrument passage and indicates deviation off of the zero-flux "glidepath." Therefore, the magnetometer 34 provides corrective information to re-align the instrument 12 to the glidepath to the target 14.

Figure 8:
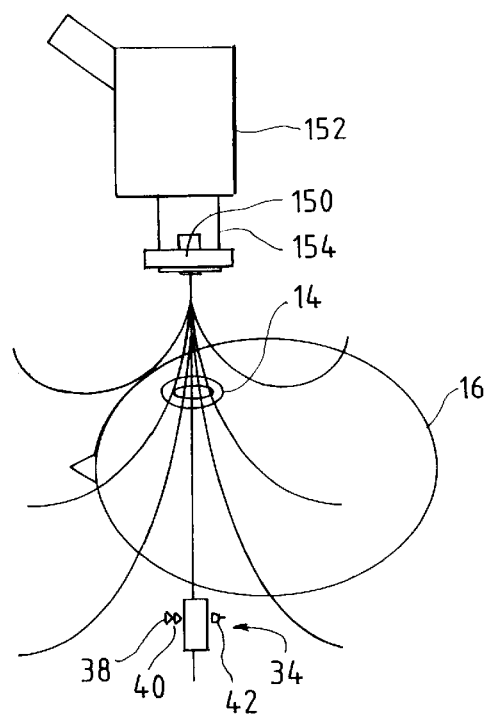
FIG. 8 is a variation of the guidance system for a surgical instrument according to the present invention.

A variation of the above system is shown in FIG. 8, which shows the system 10 with a magnet 150. Like elements in FIG. 8 have identical numbers as their counterparts in FIG. 1. The system 10 allows the alignment of an instrument such as a microscope 152 over the target area 14. The microscope 152 has a straight portion which is a cylindrical lens 154. The lens 154 is guided over the target area 14 as will be described below. The magnet 150 is a circular magnet that is mounted around the lens 154.

This orientation of the magnet 150 results in a zero-flux line pattern as shown in FIG. 8. In this embodiment, the x-plane and y-plane transducers 38 and 40 of the magnetometer 34 measure the deviation of the microscope 152 and the magnet 150 from a position parallel to the flux lines emulating from the magnet 150. The orientation of the magnet 150 results in detecting a zero-flux line when the x- and y-plane transducers 38 and 40 in the magnetometer 34 read zero field strength because they are perpendicular to the flux line. Conversely, the z-plane transducer 42 will measure full strength of the flux line as it is parallel and coincident to it. The proximity of the magnet 150 to the magnetometer 34 to the target 14 in the cranium 16 is thus derived from the increasing strength of the magnetic field as measured by the z-plane transducer 42.

Similar to the guidance display 60 shown in FIG. 4, the guidance display in this embodiment relies on the measurements from the x-plane and y-plane transducers 38 and 40. The x-position and y-position cross hairs have an intersection representing the actual position of the magnet 150 and hence the lens 154 of the microscope 152. The x-position cross hair is derived from the magnitude of the magnetic field sensed by the x-plane transducer 38. Conversely, the y-position cross hair is derived from the magnitude of the magnetic field sensed by the y-plane transducer 40.

This variation has the advantage that it is unnecessary to rotate the magnet 150 in order to obtain the x- and y-plane zero-flux line position of the tip of the instrument 12. A microscope 152 may be aligned to the target 14. The microscope may be placed to determine the exact point of entry to reach the target 14. The alignment of the magnet 150 results in severe curvature of trajectories to a target when the instrument 12 is at some distance laterally removed from the magnetometer 34.

Figure 9:
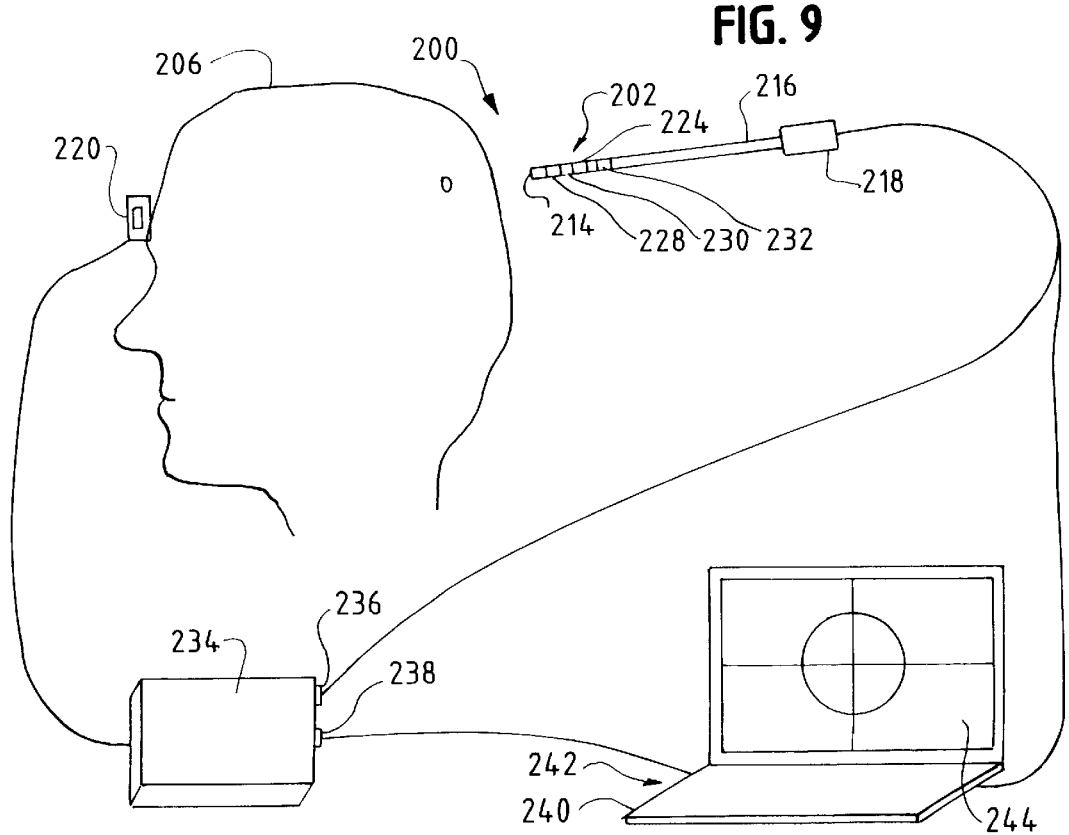
FIG. 9 is a block diagram of an alternative embodiment of the present invention.

An alternative embodiment of the present invention is shown in FIG. 9, which shows a guidance system 200 that is similar to system 10 in FIG. 1 but that reverses the respective positions of the magnet and the magnetometer. The guidance system 200 is used to guide an instrument 202 to a target location 204 within a patient's cranium 206.

The instrument 202 has a tip 214 that is inserted in the cranium 206. The instrument 202 has a straight shaft 216 that has one end coupled to the tip 214. The other end of the shaft 216 is coupled to an endoscope camera 218. An electromagnet 220 is placed on the scalp in the midline antereorly above the bridge of the nose (glabella) on the cranium 206. A magnetometer 224 is placed in the tip 214 of the instrument to detect the emitted magnetic field from the magnet 220. The instrument 202 is an endoscope in this example, though instruments of any shape may be used with the system 200 of the present invention.

The magnetometer 224 has a transducer array 226 having concentric x-, y-, and z-plane transducers 228, 230 and 232. Each transducer 228, 230 and 232 senses magnetic field strength in a different plane. The magnetometer 224 is a magnetometer tip that is manufactured by Biosense, Cordis-Webster, a division of Johnson and Johnson of New Brunswick, N.J.

The magnetometer 224 is coupled to a data interface device 234 via a data input 236. The data interface 234 is capable of real-time earth magnetic field measurement and subtraction from the emitted magnetic field of a magnet. The data taken from the magnetometer 234 is output via a data output port 238.

The data interface device 234 is coupled to a computer 240 via a RS232 port 242. The interface device 234 controls sampling of the x-, y-, and z-sense transducers 228, 230 and 232 of the magnetometer 224 of the magnetic field from the magnet 220. The computer 240 is also coupled to the output of the endoscope camera 218. The computer 240 is coupled to a display device 244 and includes appropriate software and hardware to generate the screen display similar to that shown in FIG. 4.

The guidance system 200 allows exact accuracy on the zero-flux line since the miniaturized magnetometer 224 is housed in the tip 214 of the instrument 202. Additionally, this embodiment allows either a straight or curved instrument to be used since the magnetometer 224 is located directly at the tip 214 and thus it is unnecessary to compensate for the distance between it and the tip. The alternative embodiment may be used with flexible tip instruments such as a steerable fiberscope. The location of the magnet 220 outside of the patient allows the magnet and hence the magnetic field to be stronger and thus more measurable.

Figure 10:
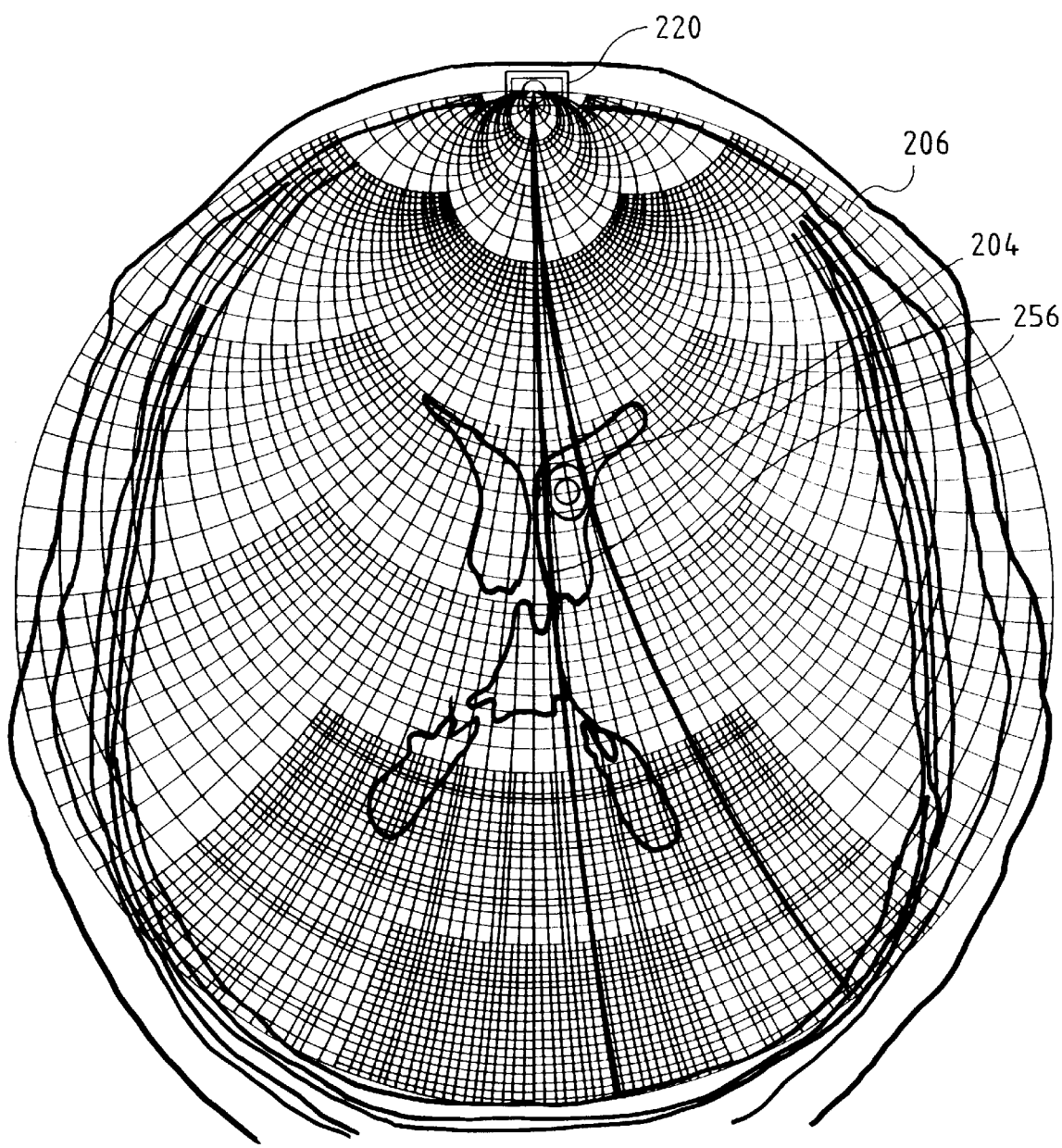
FIG. 10 is an axial MRI scan of a brain showing a target area, a family of "zero-flux lines" converging toward the target area and a magnetometer using the alternative embodiment of the present invention.
Figure 11:
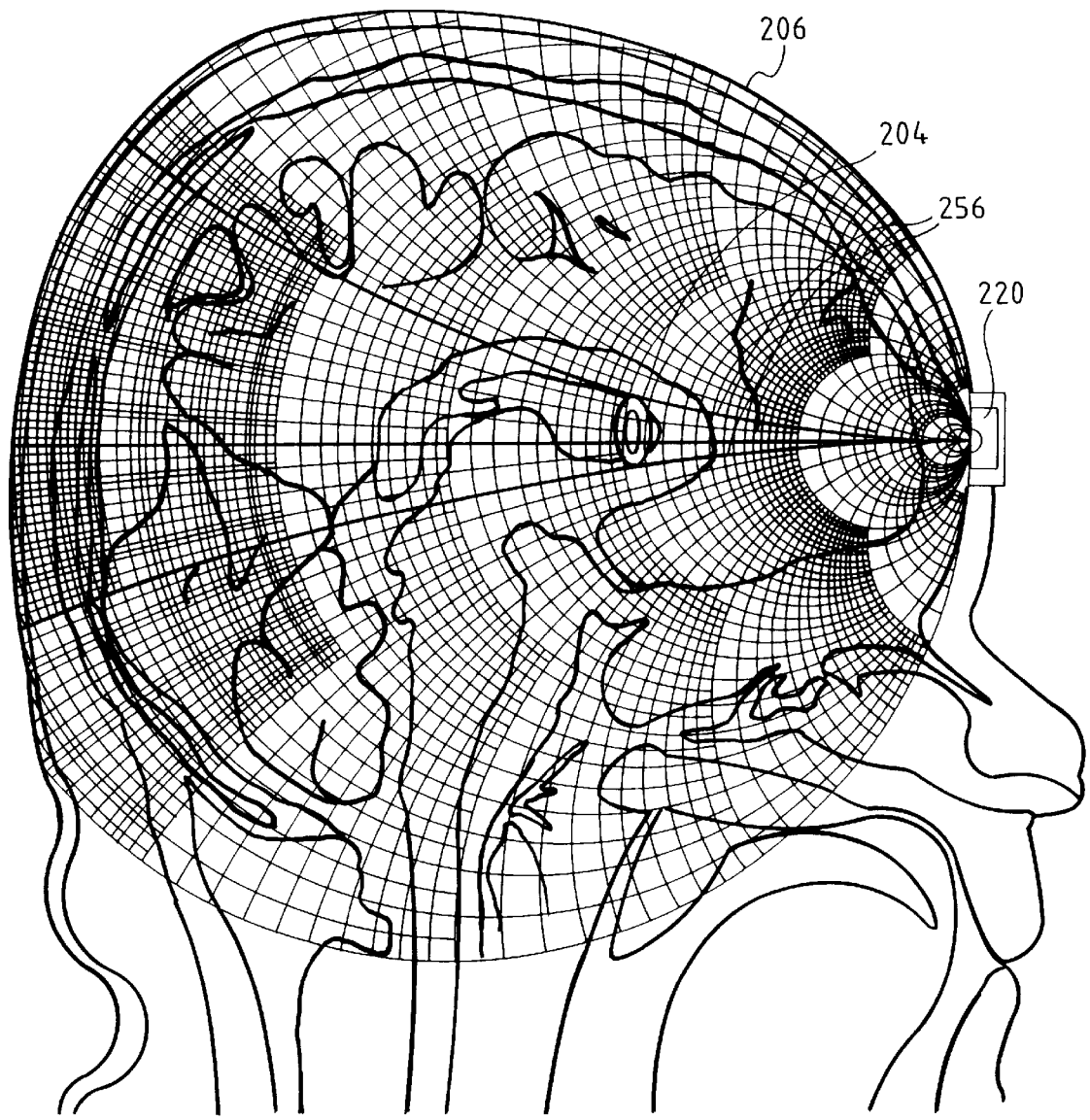
FIG. 11 is a sagittal MRI scan of a brain showing the target area, "zero-flux lines," and magnetometer of FIG. 10.

FIGS. 10 and 11 show typical views of an MRI scan of the brain in axial and sagittal orientations respectively in conjunction with the guidance system 200. In FIGS. 10 and 11 the target 204 is in the frontal horn of a lateral ventricle of the cranium 206. Flux lines emanating from the magnet 220 and zero-flux lines 256 have been superimposed to illustrate a family of convergent paths that may be selected for an appropriate burr hole to guide the instrument 12 forward toward the magnet 220. On inspection, a converged set of lines intersecting the target in the frontal horn may be readily identified. Posteriorly there is a wide selection of potential entry sites that follow a zero-flux line toward the target up-field from the magnet.

The scans in FIGS. 10 and 11 demonstrate convergence toward the target when the magnet 220 has been placed on the forehead. This is shown for illustrative purposes only as the magnet 220 may be placed in any convenient site in or on the tissue in approximate alignment with the target 204. A family of zero-flux lines 256 indicating a wide range of potential cranial entry sites converge upon and within the borders of the target area.

The instrument 202 and attached magnetometer 224 may be advanced along any of the zero-flux lines 256 as measured by the magnetometer 224. The measured flux lines are used for a visual display similar to FIG. 4 to guide the instrument 202 along a suitable glidepath.

It will be apparent to those skilled in the art that various modifications and variations can be made in the method and system of the present invention without departing from the spirit or scope of the invention. Thus, the present invention is not limited by the foregoing descriptions but is intended to cover all modifications and variations that come within the scope of the spirit of the invention and the claims that follow.

What is claimed is:

1. A guidance system for determining a path to a target area within a volume, the system comprising:
   an instrument having a substantially straight portion and a tip;
   a magnet emitting a magnetic field with a family of zero-flux lines perpendicular to isogaussian planes, wherein a selected zero-flux line is intersectable with the target area and serves as a path for the instrument and the magnet is mountable on the straight portion of the instrument;
   a magnetometer capable placed in or on a remote site in approximate alignment with the target area and the selected zero-flux line, the magnetometer including a transducer array having a x-plane transducer, a y-plane transducer and a z-plane transducer; and
   a guidance circuit coupled to the transducer array which indicates when the magnet deviates from the selected zero-flux line.

2. The guidance system of claim 1 wherein the magnet has a magnetic center and the system further comprising a self-centering housing coupled to the substantially straight portion of the instrument and holding the magnet such that the magnetic center of the magnet is aligned with the instrument.

3. The guidance system of claim 2 wherein the self-centering housing further includes an annular snugging ring which is positioned around the substantially straight portion, and wherein the housing is removable by loosening the snugging ring.

4. The guidance system of claim 2, wherein the magnet is a horseshoe magnet having two arms each with a magnetic pole, the two arms located parallel to the substantially straight portion of the surgical instrument.

5. The guidance system of claim 2 further comprising a display coupled to the guidance circuit, the display showing the tip of the instrument in relation to the target.

6. The guidance system of claim 5 wherein the display is a liquid crystal display.

7. The guidance system of claim 5 wherein the display is a cathode ray tube display.

8. The guidance system of claim 1 wherein the guidance circuit further comprises a distance circuit to determine the distance to the target area by measuring field strength emitted by the magnet perpendicular to the zero-flux line by the magnetometer.

9. The guidance system of claim 1 wherein the transducers are concentrically mounted within the magnetometer.

10. The guidance system of claim 1, wherein the transducers are mounted in-line within the magnetometer.

11. The guidance system of claim 1, wherein the transducers are fluxgate transducers.

12. The guidance system of claim 1, wherein the transducers are magneto-resistive sensors.

13. The guidance system of claim 1, wherein the magnet is manufactured from alnico, ceramic or rare earth.

14. The guidance system of claim 1 wherein the magnet is an electromagnet.

15. The guidance system of claim 14, wherein the electromagnet is energized by a dc current, pulsed dc current, or ac current.

16. The guidance system of claim 1 further comprising a compensation circuit which zeroes the magnetometer for static effects of earth's field and any ferromagnetic or electromagnetic dc effects by subtracting the flux offsets in x, y, and z plane transducers of the magnetometer to zero.

17. The guidance system of claim 1 further comprising a motor coupled to the magnet and wherein the instrument has a center axis and the magnet is rotated about the center axis of the instrument to create an alternating magnetic field.

18. The guidance system of claim 1 wherein the instrument is an endoscope.

19. A guidance system for determining a path to a target area within a volume, the system comprising:
   an instrument having a substantially straight portion and a tip;
   a magnet emitting a magnetic field with a family of zero-flux lines perpendicular to isogaussian planes, wherein the magnet has a magnetic center and a selected zero-flux line is intersectable with the target area and the magnet is mountable on the straight portion of the instrument;

a magnetometer capable placed in or on a remote site in approximate alignment with the target area, the magnetometer including a transducer array having a x-plane transducer, a y-plane transducer and a z-plane transducer;

a guidance circuit coupled to the transducer array which indicates when the magnet deviates from the selected zero-flux line;

a self-centering housing couplable to the substantially straight portion of the instrument and holding the magnet such that the magnetic center of the magnet is aligned with the instrument; and a display coupled to the guidance circuit, the display showing the tip of the instrument in relation to the target wherein the display includes:

a set of cross hairs having an intersection representing the target area location;

a set of an x-position cross hair and a y-position cross hair having an intersection representing an actual position of the instrument tip, the x-position cross hair derived from the magnitude of the field sensed by the z-plane transducer when the magnetic field flux from the magnet is measured at a maximum by the x-plane transducer and the magnetic field flux from the magnet is measured at a minimum by the y-plane transducer, and the y-position cross hair derived from the magnitude of the field from the magnet sensed by the z-plane transducer when the magnetic field flux from the magnet is measured at a maximum by the y-plane transducer and the magnetic field flux from the magnet is measured at a minimum by the x-plane transducer.

20. A method of guiding an instrument to a target area within a volume, the method comprising the steps of:

affixing a magnetometer having x-, y- and z-plane transducers within or upon the volume surface in approximate alignment with the target area and an anticipated trajectory from an outside fixed entry site;

attaching a magnet emitting a magnetic field to the instrument;

selecting a path to the target area by selecting a zero-flux line from the magnetic field which intersects the target area;

inserting the instrument into the tissue at a fixed entry site; and moving the instrument to the target area by measuring the flux lines of the magnetic field.

21. The method as claim 20 further comprising the step of zeroing the magnetometer for static effects of the earth's field and ferromagnetic or electromagnetic dc effects by placing the instrument with the attached magnet at a distance from the entry site and subtracting flux offsets in x-, y-, and z-plane transducers of the magnetometer to zero.

22. The method of claim 20 further comprising the step of overlaying imaging scans of the body with a pattern of isogaussian flux planes in the axial, sagittal, or coronal planes to define a family of zero-flux lines converging on the affixed magnetometer.

23. A method of guiding an instrument to a target area within tissue the method comprising the steps of:

affixing a magnetometer having x-, y- and z-plane transducers within or upon the tissue surface in approximate alignment with the target area and an anticipated traiectory from an outside fixed entry site;

attaching a magnet emitting a magnetic field to the instrument;

inserting the instrument into the tissue at a fixed entry site;

determining the location of the instrument relative to the target area by measuring the flux lines of the magnetic field; and zeroing the magnetometer for static effects of the earth's field and ferromagnetic or electromagnetic dc effects by placing the instrument with the attached magnet at the fixed entry site in approximate visual orientation toward the target area and magnetometer and subtracting flux offsets in x-, y-, and z-plane transducers of the magnetometer to zero.

24. The method of claim 23 wherein the step of inserting the instrument further comprises selecting an intersecting zero-flux line extending from the entry site and converging on the magnetometer and the target area.

25. The method of claim 24 further comprising the steps of:

displaying the target area;

displaying the actual position of the instrument in relation to the target area;

providing a feedback display to enable correction of the position of the instrument to overlie the selected zero-flux trajectory line.

26. The method of claim 25 further comprising the step of displaying a 3-dimensional display of the depth of passage along the zero-flux trajectory line to the target area.

27. The method of claim 26, wherein the 3-dimensional display is rendered as enlarging concentric circles until the target area is intersected by the instrument.

28. The method of claim 27, wherein the step of determining the location includes the steps of:

rotating the magnet;

deriving the x-axis location of the instrument from the magnitude of the field sensed by the z-plane transducer when the magnetic field flux is measured at a maximum by the x-plane transducer and the magnetic field flux is measured at a minimum by the y-plane transducer; and deriving the y-axis location of the instrument from the magnitude of the field sensed by the z-plane transducer when the magnetic field flux is measured at a maximum by the y-plane transducer and the magnetic field flux is measured at a minimum by the x-plane transducer.

* * * * *